(12) United States Patent
Bonaccorsi et al.

(10) Patent No.: US 8,431,684 B2
(45) Date of Patent: Apr. 30, 2013

(54) PROCESS FOR THE PREPARATION OF IBODUTANT (MEN15596) AND RELATED INTERMEDIATES

(75) Inventors: Fabrizio Bonaccorsi, Leghorn (IT); Valentina Fedi, Campi Bisenzio (IT); Danilo Giannotti, Altopascio (IT)

(73) Assignee: Malesci Istituto Farmacobiologico S.p.A., Bagno A Ripoli (IT)

( * ) Notice: Subject to any disclaimer, the term of this patent is extended or adjusted under 35 U.S.C. 154(b) by 0 days.

(21) Appl. No.: 13/321,501

(22) PCT Filed: May 11, 2010

(86) PCT No.: PCT/EP2010/002884
§ 371 (c)(1),
(2), (4) Date: Nov. 18, 2011

(87) PCT Pub. No.: WO2010/133306
PCT Pub. Date: Nov. 25, 2010

(65) Prior Publication Data
US 2012/0065370 A1    Mar. 15, 2012

(30) Foreign Application Priority Data
May 21, 2009  (IT) .............................. MI2009A0897

(51) Int. Cl.
*A61K 38/06*   (2006.01)
(52) U.S. Cl.
USPC ...................................................... 530/331

(58) Field of Classification Search ............ 530/331
See application file for complete search history.

(56) References Cited

FOREIGN PATENT DOCUMENTS
WO    WO 03/037916 A2    5/2003

OTHER PUBLICATIONS

Valentina Fedi, et al., "Discovery of a New Series of Potent and Selective Linear Tachykinin $NK_2$ Receptor Antagonists", Journal of Medicinal Chemistry, 50(20), 4793-4807 CODEN: JMCMAR; ISSN 0022-2623, 2007, XP002555255 cited in the application p. 4794, left-hand column—p. 4796, left-hand column; compound 48F, Sep. 2007.

Alessandro Sisto, et al., "α,α-Cyclic aminoacids as useful scaffolds for the preparation of $hNK_2$ receptor antagonists", Bioorganic & Medicinal Chemistry Letters, 17(17), 4841-4844 CODEN: BMCLE8; ISSN: 0960-894X, 2007, XP022184920, Jun. 2007.

*Primary Examiner* — John Mabry
(74) *Attorney, Agent, or Firm* — Arent Fox, LLP

(57) ABSTRACT

This invention relates to a novel process for synthesizing the product ibodutant shown in the figure below, consisting of a small number of high-yield steps involving reagents and solvents with low environmental impact, characterized by the coupling of two portions, compounds (3) and (4), one of which (3) is synthesized by coupling of 6-methyl-2-benzo[b]thiophenecarboxylic acid (1) with 1-amino-alpha-alpha-cyclopentan carboxylic acid and subsequent cyclization with oxazolone, while the other, compound (4), is obtained from suitable highly selective functionalizations of 4-aminomethylpiperidine (2).

7 Claims, 1 Drawing Sheet

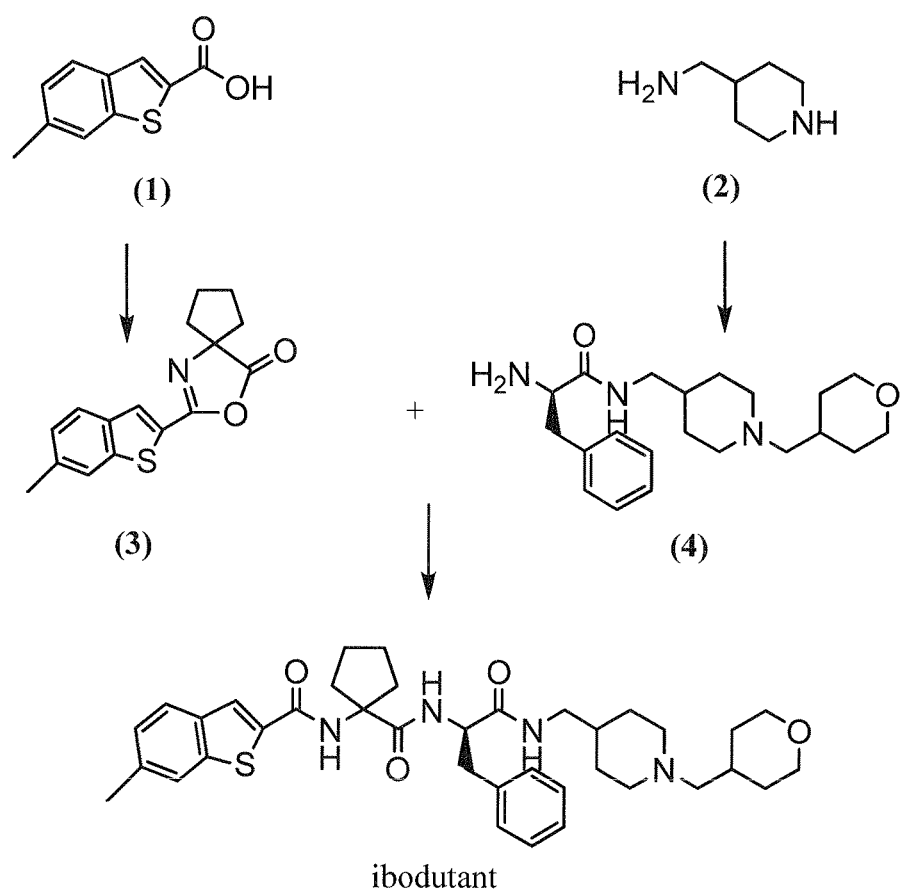

PROCESS FOR THE PREPARATION OF IBODUTANT (MEN15596) AND RELATED INTERMEDIATES

CROSS-REFERENCE TO RELATED APPLICATION

This application is a National Stage entry of International Application No. PCT/EP2010/002884, filed May 11, 2010, which claims priority to Italian Patent Application No. MI2009A000897 filed May 21, 2009. The disclosures of the prior applications are incorporated in their entirety by reference.

FIELD OF INVENTION

This invention relates to a novel process for the synthesis of ibodutant (MEN15596), a product which possesses tachykinin NK2 receptor antagonist activity.

Said process is based on highly efficient syntheses of the two precursors (3) and (4), conducted with methods and reagents suitable for production on an industrial scale.

In particular, the process involves the use of 4-aminomethylpiperidine which is functionalized with a high degree of selectivity on the primary amine alone, by acylation, or the secondary amine alone, by transient acylation, and subsequent alkylation under reductive amination conditions. These strategies allow a reduction in the total number of steps, while obtaining intermediates of superior quality to those already reported. Moreover, the procedures reported herein produce key intermediates with far higher yields, and consequently give rise to a synthesis process which is far more economical on the whole than those previously reported.

The invention also includes an alternative method of synthesising (1) by hydrodehalogenation of the corresponding 3-chloro-derivative under Pd-catalysed catalytic hydrogenation conditions.

STATE OF THE ART 6-methyl-benzo[b]thiophene-2-carboxylic acid [1-(2-phenyl-[(R)-{[1-(tetrahydro-pyran-4-ylmethyl)-piperidin-4-ylmethyl]-carbamoyl}-ethylcarbamoyl)-cyclopentyl]-amide, known as "ibodutant" (MEN 15596), is a compound with a potent tachykinin $NK_2$ receptor antagonist activity, and can therefore be used to prepare pharmaceutical compositions for the treatment of disorders involving tachykinins, and in particular neurokinin A.

Said compound and some intermediates thereof are disclosed in patent WO03037916. In particular, Example 139 discloses the synthesis of the product according to the description given in example 117 of said patent (Scheme 1).

Said document obtains the end product by methods known to one skilled in the art, first by sequentially attaching Boc-cycloleucine to intermediate (4), then deprotecting the Boc by the usual methods, and finally acylating intermediate (15) thus obtained with the acyl chloride of intermediate (1). In said patent, the intermediate 2-(R)-amino-3-phenyl-N-[1-(tetrahydro-pyran-4-ylmethyl)-piperidin-4-ylmethyl]-propionamide (4) is obtained by the following procedure. 4-tetrahydropyrancarboxylic acid methyl ester (5) is hydrolysed to (6) under basic conditions, then converted to the corresponding acyl chloride (7), and reacted with 4-carbethoxypiperidine (8).

Scheme 1

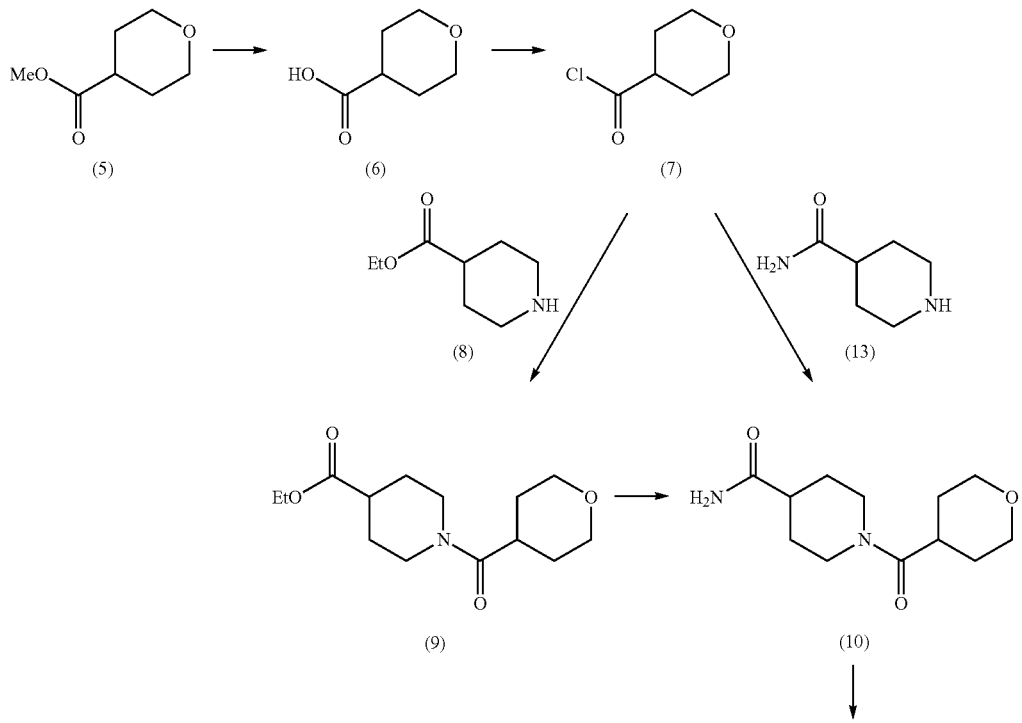

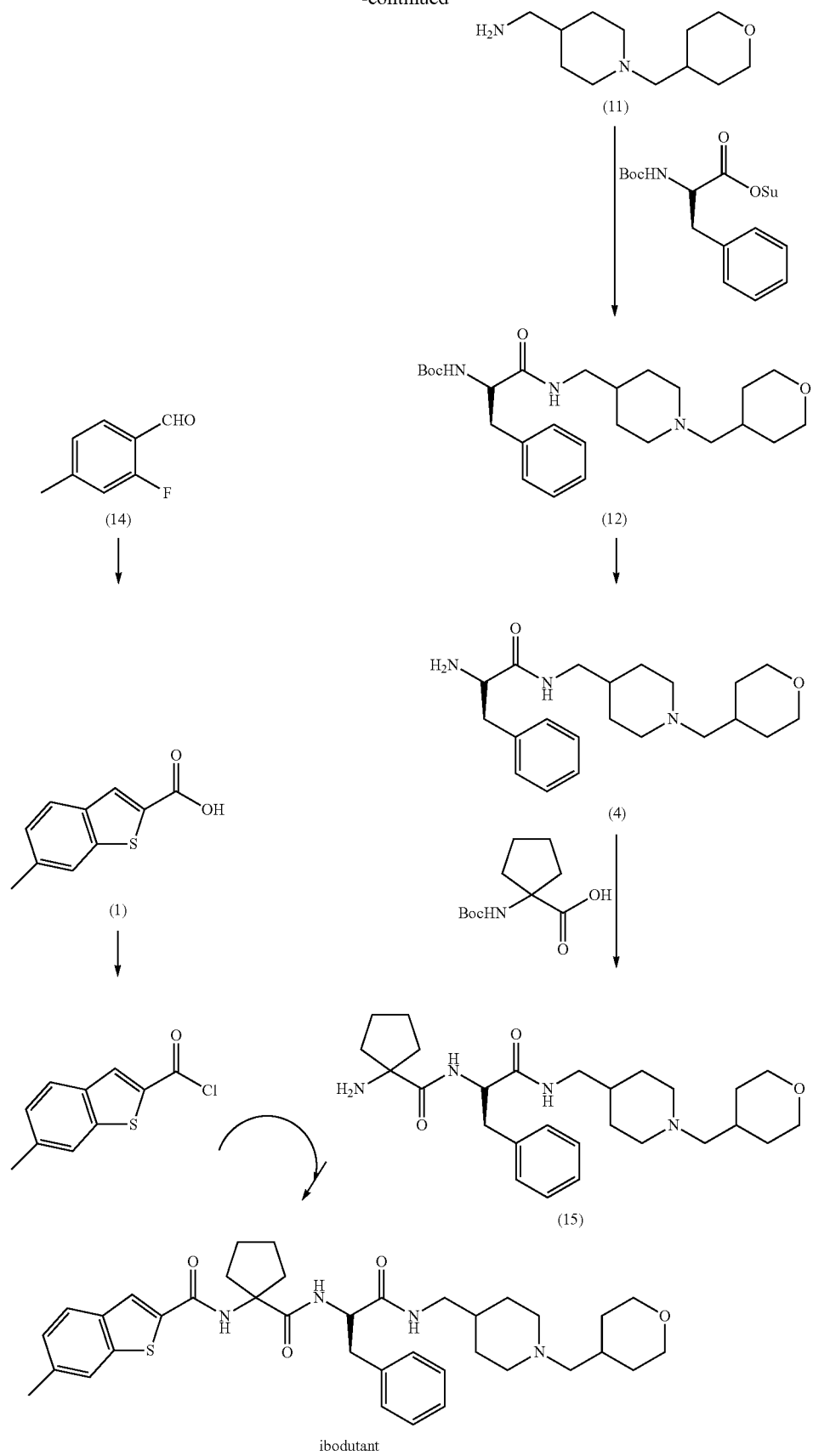

Adduct (9) is then treated with ammonia to give the corresponding primary amide (10). Said diamide intermediate displays a marked affinity for water, and is therefore difficult to isolate by extraction in organic solvent (see WO03037916, paragraph 30, p. 45, wherein 25 extractions with chloroform are reported, and J. Med. Chem. 2007, 50, 4793-4807, p. 4806 (synthesis of compound 45), wherein 18 extractions with DCM (dichloromethane) to obtain a 70% yield are reported). Its two amide functions (primary and tertiary) are simultaneously reduced by treatment with borane (a reagent unsuitable for industrial use) in THF (tetrahydrofuran) to give the corresponding diamine. The diamine (11) thus obtained is reacted with Boc-D-Phe-OSu, and adduct (12) is then deprotected by standard methods to give (4). No less than 7 steps are therefore required to obtain key intermediate (4) with this procedure.

The same patent also describes in general form, and specifically with reference to compounds other than ibodutant, methods involving the use of oxazolone structures (WO03037916, pp. 14-15) similar to intermediate (3) of the present invention (Figure).

A further synthesis of the product in question is reported in the study J. Med. Chem., 2007, 50, 4793-4807 (Scheme 1), which indicates, as a substantial difference from the synthesis described in the above-mentioned patent, that amine portion (11) is obtained by reacting acyl chloride (7) of 4-tetrahydropyrancarboxylic acid directly with isonipecotamide (13) in the presence of triethylamine in mixed DCM/DMF solvent, and subsequently reducing diamide (10) with LiAlH4 in THF. Said modification reduces from 7 to 6 the number of steps required to obtain (4), but still involves too many synthesis steps, some of which are performed in solvents, such as DMF, which involve toxicity and disposal problems unacceptable in large-scale production, and the presence of particularly hazardous reagents such as LiAlH$_4$. As the skilled person would be aware, reduction treatment with LiAlH$_4$ also involves as a side effect the formation, which cannot be excluded, of the product of dealkylation at the level of partial reduction of the tertiary amide which contaminates intermediate (11) through the presence of 4-aminomethylpiperidine.

As regards the methods of obtaining 6-methyl-2-benzo[b]thiophenecarboxylic acid (1), the study J. Med. Chem., 2007, 50, 4793-4807 indicates, as the general procedure, one of the possible syntheses, starting with 2-fluoro-4-methylbenzaldehyde, for treatment with methyl thioglycolate under conditions of aromatic nucleophilic substitution in the presence of basic conditions (Cs$_2$CO$_3$, DMSO) slightly different from those reported in the literature (J. R. Beck et al., J. Org. Chem. 1972, 37, 3224-3226, A. J. Bridges, Tetrahedron Lett. 1992, 33, 7499-7502). The first of the above two studies describes the synthesis of 2-benzo[b]thiophenecarboxylic acid esters from 2-nitro-benzonitriles or 2-nitrobenzaldehydes by treatment with methyl thioglycolate, KOH in DMF, and methyl thioglycolate K$_2$CO$_3$ and DMF, respectively, with highly variable yields, depending on the substrates used. The second study reports the synthesis of 2-benzo[b]thiophenecarboxylic acid esters from 2-fluorobenzaldehydes by treatment with methyl thioglycolate, with triethylamine or NaH in DMSO, with equally variable temperatures and yields, depending on the substrates used. Although intermediate (1) is obtained by this process with a good yield and good quality, the process is not very robust in the event of minor time and temperature changes or variations in the order in which the reagents are added, and these factors prevent its large-scale application.

Again with regard to the synthesis of 6-methyl-2-benzo[b]thiophenecarboxylic acid, other synthesis methods are also reported in the literature, as general methods for obtaining 2-benzo[b]thiophenecarboxylic acids: a) J. Heterocyclic Chem. 1975, 12, 889-891 and J. Heterocyclic Chem. 1983, 20, 55-59, according to which suitably functionalised benzaldehydes are reacted with rhodanine and hydrolysed under basic conditions with the corresponding cinnamic mercapto-acids, which are induced to cyclise to the corresponding benzo[b]thiophenes by hot oxidation treatment with iodine in a suitable solvent; b) WO03106462 and Org. Proc. Res. Dev, 2006, 10, 296-303 according to which variously functionalised 2-benzo[b]thiophenecarboxylic acids are obtainable (by carboxylation) from the corresponding benzothiophenes, which are obtained from benzenethiols (functionalised in the meta and para position) by alkylation with bromoacetaldehyde diethyl acetal and subsequent cyclisation, for example with polyphosphoric acid in toluene; these syntheses are also unsatisfactory for industrial use.

The 2-carboxy-benzo[b]thiophene hydrochloride compounds in position 3 are known in the literature, starting from the corresponding cinnamic acids, by oxidation with thionyl chloride in the presence of catalytic amounts of a base like pyridine (J. Org. Chem. 1975, 40, 3037-3045) or DIMAP (WO95/15323). No studies regarding the possibility of hydrodehalogenating these carboxylic acids (as such or in the form of salts) to remove the chlorine have been found; however, reductions of esters or amides which often involve particularly drastic conditions (not applicable on a large scale) are known, such as the use of Ni Raney (on amides, WO9534551), Pd black as catalyst, or high hydrogen pressures. For example, the reduction of 3-chloro-2-benzothiophenecarboxylic acid esters is reported in Helv. Chim. Acta, 1994, 77, 100-110, by hydrogenation with Pd/C in the presence of bases such as triethylamine or AcONa, with very poor yields.

On the basis of the findings in the literature available to date, the synthesis of the compound ibodutant therefore still presents numerous problems. There is consequently a strongly felt need to develop a novel synthesis process suitable for industrial use.

SUMMARY

The Applicant has now surprisingly found a novel and more efficient process for the synthesis of ibodutant, which is summarised in Scheme 2.

Said process eliminates the drawbacks already described for the previously known synthesis routes, as follows:

i) it reduces the large number of synthesis steps: intermediate (4) is obtained with only 3 steps (instead of 7 or 6), conducted with high yields, and consequently produces an evident advantage in the economy of the entire synthesis process that leads to ibodutant. Intermediate (12) is obtained with yields of between 95% and 80%, as against the 45% yield previously described (see J. Med. Chem., 2007, 50, 4793-4807). The product thus obtained is also qualitatively better.

ii) it limits the use of solvents not ideal for industrial synthesis such as DMF, which is teratogenic, high-boiling and miscible with water (reflux), in favour of solvents which are innocuous, such as isopropanol, low-boiling, such as THF, and/or immiscible with water, such as DCM or AcOEt (ethyl acetate).

iii) it avoids the need to use highly dangerous hydride reducers such as BH$_3$ in THF or LiAlH$_4$, replacing them, in order to obtain compound (12), with the more manageable Na(AcO)$_3$BH with reductive amination reactions.

iv) it eliminates the passage through the diamide intermediate (scheme 1, compound (10)), which is highly soluble in water, and therefore difficult to extract, isolate and analyse.

v) in the case of acylation of diamine (11), the use of Boc-D-Phe-OSu is also avoided by substitution with the corresponding unactivated aminoacid and activation in situ using methods well known to the skilled person, such as isobutyl chloroformate or carbonyldiimidazole, producing a considerable cost saving which has a significant impact on the total cost of the entire manufacturing process of the active ingredient.

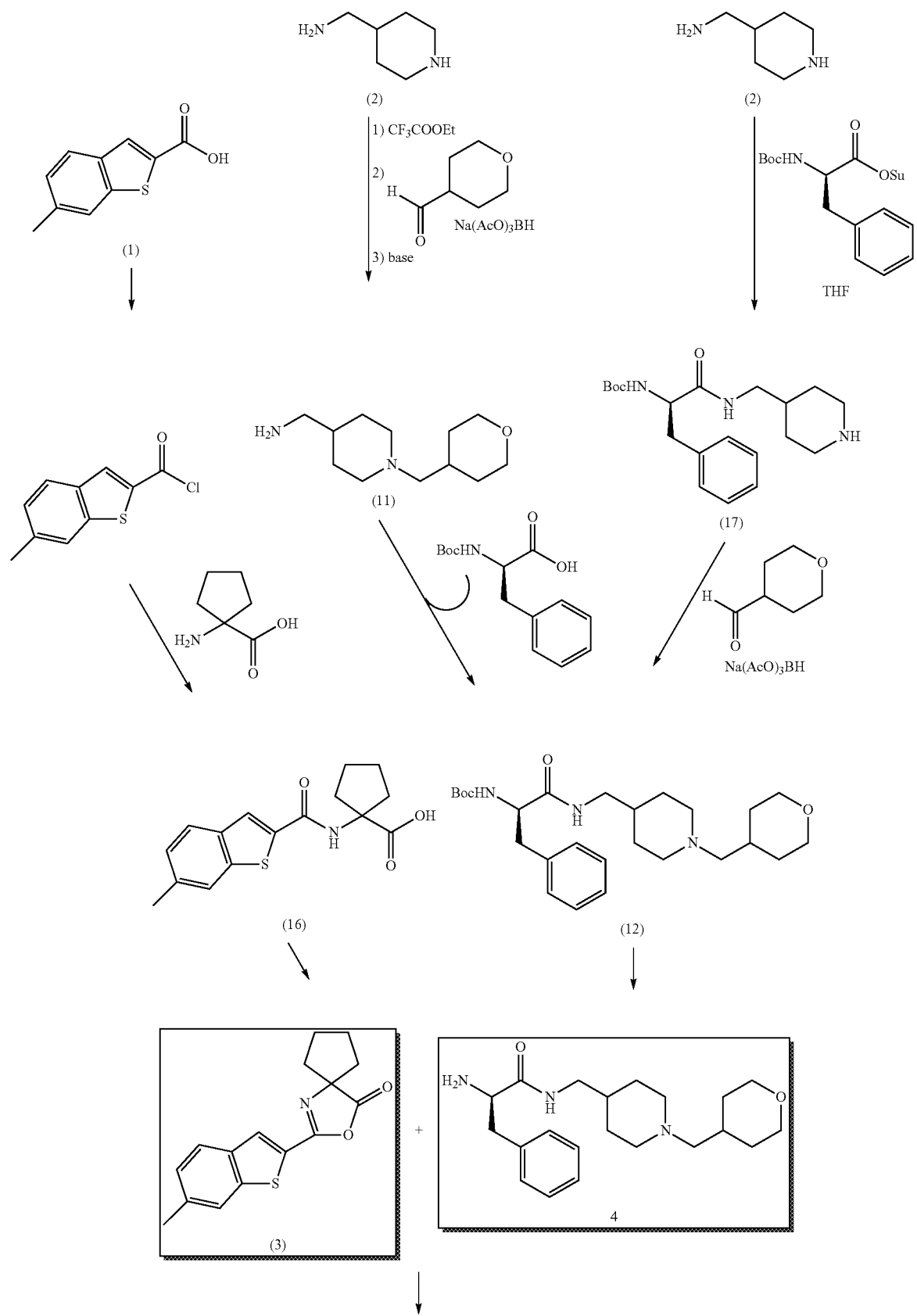
Scheme 2

-continued

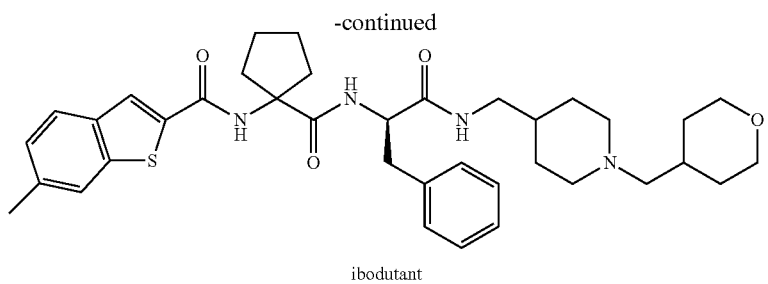

ibodutant vi) surprisingly, 6-methyl-2-benzo[b]thiophenecarboxylic acid (1) can be prepared by catalytic hydrogenation directly from the corresponding 3-chloro acid (18) with high yields, and procedures and reagents suitable for production on an industrial scale. (Scheme 3)

vii) and finally, the converging synthesis thus performed produces ibodutant with yields far exceeding those obtained with the systems previously described (yield of intermediate (12): method according to J. Med. Chem., 2007, 50, 4793-4807: 60%; method described by analogy in WO03037916: <55%; method to which this invention relates: between 85% and 90%).

Scheme 3

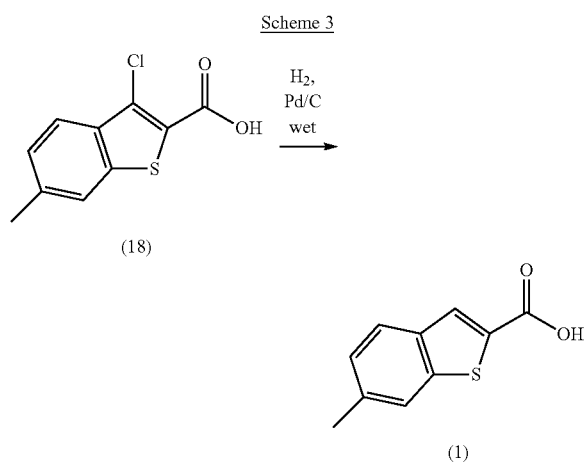

The present invention therefore relates to a method for obtaining the compound ibodutant which is suitable for industrial use, characterised by coupling of the two intermediates (3) and (4), wherein intermediate (3) is obtained from 6-methyl-benzothiophenecarboxylic acid, and only optionally isolated, and intermediate (4) is obtained by deprotecting compound (12), suitably obtainable from 4-aminomethyl piperidine (2).

Diamine (11) is obtainable from 4-aminomethyl piperidine (2), using the one-pot procedure, by selective protection of the primary amine function, reductive amination with 4-tetrahydropyranaldehyde, and hydrolysis under basic conditions. The diamine thus obtained is reacted with suitably activated Boc-D-Phe-OH to give intermediate (12), which is deprotected to intermediate (4).

Alternatively, compound (4) can be obtained, again from 4-aminomethylpiperidine (2), by selective acylation with Boc-D-Phe-OSu followed by reductive amination with 4-tetrahydropyranaldehyde to give intermediate 12, which is deprotected to intermediate 4.

Another subject of the present invention is the synthesis of compound (1) starting with 3-chloro-benzothiophene-2-carboxylic acid (18) by simple hydrodehalogenation catalysed by Pd/C.

DETAILED DESCRIPTION OF THE INVENTION

According to the present invention, the compound ibodutant is obtained by the method described in Scheme 2, starting from intermediates (3) and (4).

Intermediate (4) is obtained from 4-aminomethylpiperidine (2), preferably according to the following procedure: diamine (2) is dissolved in a solvent selected from DCM, EtOH, iPrOH (isopropanol), $CH_3CN$, DME (dimethoxyethane) and dioxane, among which iPrOH is preferred, the solution obtained is maintained at a temperature of between −20° and +20° C., preferably between −10 and +5° C., and even more preferably at 0° C., and ethyl trifluoroacetate (1-1.2 eq, preferably 1.1 eq) is added. When protection is complete, 4-formyl-tetrahydropyran (1-1.7 eq., preferably 1-1.2 eq) is added, and the solution is diluted and then reflux heated to allow evaporation of the ethanol and part of the water present as by-products of acylation and condensation between the amine and aldehyde respectively. This means that the subsequent operations of adding the reducing agent and reducing the excess reducing agent required to effect complete conversion are more manageable. Sodium triacetoxyborohydride ($NaBH(AcO)_3$, 1-2 eq., preferably 1-1.2 eq) is then added in portions to the solution at a temperature of between −20° C. and +60° C. The solution is then adjusted to ambient temperature and when alkylation is complete, aqueous NaOH is added to neutralise the reducing agent and hydrolyse the trifluoroacetamide to intermediate (11). The mixture is reflux heated and then concentrated. Intermediate (11) is then extracted in DCM and can be isolated by evaporation, or preferably used directly for the next step, possibly with a single concentration step or solvent change treatment.

To obtain intermediate (12) it is sufficient to react an activated form of aminoacid Boc-D-Phe-OH, by methods known to the skilled person, with intermediate (11) described above. The procedure disclosed, by way of example but not of limitation, involves suspending Boc-D-Phe-OSu in a non-protic organic solvent, preferably selected from DCM and THF, and adding it portionwise at a temperature of between −10° and +30° C., preferably between +10° and +20° C., to the solution of (11), also dissolved in a suitable solvent, preferably selected from DCM and THF.

Alternatively, Boc-D-Phe-OH can be activated, again according to methods known to the skilled person, with isobutyl chloroformate (IBCF) in the presence of an organic base selected from N-methylmorpholine (NMM), diisopropylethylamine (DIPEA) and $NEt_3$ (triethylamine), preferably with NMM, at a temperature of between −30 and +10° C., preferably between −10° C. and +5° C., and even more preferably between −5° C. and 0° C., in a non-protic organic solvent preferably selected from DCM and THF, or with carbonyldiimidazole (CDI) in the same solvents at a temperature of between −10° C. and +5° C., preferably 0° C. Intermediate (11), dissolved in DCM, is added to the Boc-phenylalanine thus activated and dissolved, preferably in DCM; alternatively, the activated aminoacid solution can be added to the cooled solution of (11).

According to the present invention, intermediate (12) can alternatively be obtained by reacting 4-aminomethylpiperidine (2) dissolved in THF with the activated aminoacid, Boc-D-Phe-OSu, also suspended in THF, at a temperature of between −20° C. and +10° C., preferably between −5° C. and 0° C. Under these conditions it surprisingly becomes possible to acylate the primary amine function with high selectivity, to give mainly intermediate (17), which can be isolated by precipitation from suitable solvent mixtures, in particular from toluene/cyclohexane, and is converted to derivative (12) under reductive amination conditions, as already described, by reaction with 4-formyl-tetrahydropyran and a suitable hydride reducer, preferably NaBH(OAc)$_3$, in a solvent preferably selected from DCM (dichloromethane), THF and CH$_3$CN, and even more preferably in DCM.

Intermediate (12), obtained in accordance with the methods described in the present invention, can be crystallised from methyl ethyl ketone, AcOR, iPrOH, MeOH, MeOH/H$_2$O, 2-methyl-tetrahydrofuran, 1,2-dimethoxyethane and toluene; where R means an alkyl R1-R4, straight-chain or branched, and preferably selected from methyl, ethyl, propyl, isopropyl, butyl, sec-butyl, tert-butyl; preferably from AcOEt.

Intermediate (4) is preferably obtained by deprotecting Boc in a biphasic mixture (H$_2$O/DCM) by treatment with HCl and subsequent extraction of the aqueous phase, made basic by adding an organic or inorganic base, and preferably by adding NaOH (32%), with immiscible organic solvents, preferably DCM. Compound (4) can be crystallised from solvents such as methyl-tert-butyl-ether, cyclohexane, ethyl acetate and mixtures thereof, from mixtures of heptane/AcOEt, and preferably from cyclohexane/ethyl acetate mixtures, preferably in the ratio of 6/1.

Intermediate (3) is obtained from 6-methyl-benzothiophenecarboxylic acid (1). The carboxyl function is activated by formation of the corresponding acyl chloride with methods well known to one skilled in the art, including, by way of example but not of limitation, treatment with oxalyl chloride and catalytic DMF in a suitable solvent, preferably toluene. Said solution of the activated species is added to a solution, possibly cooled, of cycloleucine activated by silylation by known methods, such as treatment with bis-trimethylsilyl acetamide (BSA). The adduct is then hydrolysed and isolated by extractive work-up. Carboxylic acid (16) is condensed to the corresponding oxazolone (3) by known methods including, for example, treatment with ethyl dimethyl aminopropylcarbodiimide hydrochloride (EDAC) and DIPEA in THF/CH$_3$CN or treatment with IBCF and NEt$_3$, preferably in DCM or EtOH. Compound (3) can be isolated or used without isolation directly for the reaction with (4).

The two intermediates (3) and (4), obtained as described above, are reacted in a suitable solvent selected from DMF and AcOR, where R means an alkyl R1-R5, straight-chain or branched, preferably selected from methyl, ethyl, propyl, isopropyl, butyl, sec-butyl and tert-butyl, and even more preferably in AcOEt, at a temperature of between 20 and 100° C., and preferably at a temperature of 76-78° C., for a time of between 10 and 30 hours. The compound ibodutant is obtained in this way with yields of between 70 and 90% in the last step.

If necessary, the compound can be recrystallised from EtOH, EtOAc and mixtures thereof, or mixtures of EtOH and MEK (methyl-ethyl-ketone), preferably EtOH.

The present invention also relates to the process for obtaining intermediate (1) by catalytic hydrogenation of 3-chloro-6-methyl-benzothiophene carboxylic acid (18). The procedure involves the use of a Pd/C catalyst, preferably 5%, preferably wet, in a suitable solvent mixture which guarantees that the reagent and product will remain in solution, preferably with MeOH/H$_2$O mixtures, possibly with the addition of a non-protic polar solvent such as DMF or THF, and in the presence of an organic or inorganic base, preferably a hydroxide of an alkaline metal, and even more preferably NaOH. Hydrogen can be replaced by a reagent known to the skilled person as hydrogen transferor, and preferably by ammonium formate. Said process enables intermediate (1), with an excellent yield and purity, to be obtained in a single step from a cheap, commercially available product, using reagents suitable for industrial production.

EXAMPLES

Example 1

C-(1-(tetrahydropyran-4-ylmethyl)-piperidin-4-yl)-methylamine (11)

4-(aminomethyl)-piperidine (2) (11.5 g) is dissolved in isopropanol and cooled to between −10° C. and −5° C.; 15.5 g of ethyl trifluoroacetate is then added in portions, maintaining the internal temperature at under 0° C. When the addition has been completed, the reaction mixture is left under stirring at 0° C. for 1 hour. 11.6 g of 4-formyl-tetrahydropyran and further isopropanol are then added rapidly, still at 0-5° C.

The reaction mixture is reflux heated, and part of the solvent is then distilled. After cooling to 10° C., 23.4 g of sodium triacetoxy borohydride is added in portions, maintaining the temperature at under 20° C. The reaction mixture is maintained under stirring at ambient temperature for 2 hours; 52.2 g of 32% NaOH solution and 14 g of water are then added. The reaction mixture is reflux heated for 2 hours and evaporated at low pressure, eliminating part of the distillate.

The mixture is cooled to ambient temperature, and more water and methylene chloride are added. After extraction with methylene chloride the combined organic phases are washed with 2M NaOH and partly evaporated at low pressure. The solution of (11) thus obtained (content of (11) amounting to a theoretical value of 21.4 g) is normally used "as is" in the subsequent preparation of compound (12).

A sample of product (11) obtained by evaporation until dry has been characterised as reported below.

MS (ESI, positive ions), m/z: 213 [M+H]$^+$; (CAD MS/MS), m/z: 196.99

$^1$H-NMR (CDCl$_3$, 200 MHz): δ (ppm) 0.98-1.36 (m, 6H), 1.49-1.95 (m, 6H), 2.04-2.21 (m, 2 H), 2.44-2.61 (m, 2 H), 2.73-2.93 (m, 2 H), 3.22-3.45 (m, 2 H), 3.83-4.01 (m, 2 H).

Example 2

(2-phenyl-1-(R)-((1-(tetrahydropyran-4-ylmethyl)-piperidin-4-yl-methyl)-carbamoyl)-ethyl)-carbamic acid tert-butyl ester (12) (Method A)

36.5 g of Boc-D-Phe-OSu is suspended in methylene chloride (125 ml); the suspension is stirred at the temperature of approx. 15° C. and the dichloromethane solution of product (11) (21.4 g), prepared as described in example 1, is added in portions, maintaining the temperature at under 20° C.

After 2 hours' stirring at ambient temperature, an 8% solution of NaOH is added to the reaction mixture. After 30 minutes' stirring and separation of the phases, the organic phase is washed with water (2×) to obtain a dichloromethane solution containing 43.4 g of product (12).

HPLC purity: 94.1%

Crystallisation of Compound (12)

A solvent change is performed on the crude dichloromethane solution of (12) at atmospheric pressure with ethyl acetate, and the product is crystallised hot from ethyl acetate by seeding. The suspension obtained by cooling to ambient temperature is further cooled to 0° C. for approx. 2 hours and filtered. The solid on the filter is washed with a 1:1 (v/v) mixture of ethyl acetate/MTBE (methyl tertiary butyl ether) solvents. The solid is then dried under vacuum to obtain 39.4 g of (12). Yield=85.1% (starting from 4-aminomethyl piperidine)

Purity (HPLC) 100%

HPLC: Zorbax Eclipse XDB-CN column, 3.5 µm, 150×4.6 mm, mobile phase: preformed $KH_2PO_4$ 20 mM at pH 7/$CH_3CN$: 62/38. Flow rate: 1 ml/min, detector: UV, λ=214 nm, injection volume: 20 µl, temperature: 25° C.; RT (12) =13.8 minutes $^1$H-NMR (DMSO-$d_6$, 300 MHz): δ (ppm) 1.02-1.79 (m, 12H), 1.31 (s, 9H), 2.07 (d. 2H), 2.74-2.78 (m, 2H), 2.88-2.96 (m, 3H), 3.22-3.33 (m, 3H), 3.80-3.83 (m, 2H), 4.01-4.20 (m, 1H), 6.88 (dd, 1H), 7.18-7.26 (m, 5H), 7.82 (broad singlet, 1H).

Example 3

(R)-tert-butyl 1-oxo-3-phenyl-1-(piperidin-4-ylmethylamine)propan-2-ylcarbamate (17)

4-aminomethyl piperidine (2) (6.365 g) is dissolved in tetrahydrofuran. The solution obtained is cooled to between −5° C. and 0° C., and a solution containing 10 g of Boc-D-Phe-OSu is added under stirring, in portions, in approx. 2.5 hours. 30 minutes after the end of the addition, when the disappearance of the Boc-D-Phe-OSu has been verified, the temperature is allowed to rise to ambient temperature and toluene is added, washing with 10% aq. $Na_2CO_3$ (2×).

A solvent change is then performed: at low pressure, part of the toluene is evaporated, cyclohexane is added (to a toluene:cyclohexane ratio of 2:3), and the mixture is cooled at 0° C. for 2 hours. The suspension obtained is filtered and washed with cyclohexane, and the solid is stove-dried under vacuum at 45° C. to obtain 9.18 g of compound (17). Yield 92.0%

HPLC purity: 95.2%

$^1$H-NMR (DMSO-$d_6$, 200 MHz): δ (ppm) 0.84-0.98 (m, 2H), 1.24 (bs, 1H, NH), 1.30 (s, 9H,), 1.35-1.55 (m, 3H), 2.28-2.41 (m, 2H), 2.70-2.78 (dd, 1H), 2.80-3.00 (m, 5H), 4.07-4.17 (m, 1H), 6.88 (d, 1H), 7.1-7.3 (m, 5H), 7.82 (brt, 1H)

MS: m/z: 191 (M+H)$^+$

Example 4

(2-phenyl-1-(R)-((1-(tetrahydropyran-4-ylmethyl)-piperidin-4-ylmethyl)-carbamoyl)-ethyl)-carbamic acid tert-butyl ester) (12) (Method B)

Compound (17) (8.50 g) is dissolved in dichloromethane under slight nitrogen flow, and 3.10 g of 4-formyl tetrahydropyran is added to the solution obtained under stirring, at ambient temperature. After approx. 15 minutes, 6.21 g of sodium triacetoxy borohydride is added in portions.

The mixture is kept under stirring at ambient temperature overnight; a solution of 4M NaOH is then added to the reaction mixture at ambient temperature. After approx. 20 minutes' stirring the organic phase is separated and washed with water (2×). A solvent change is then effected at atmospheric pressure with ethyl acetate, and the solution is seeded with crystalline compound (12) and gradually cooled overnight. After cooling at 0° C. for 2 hours, the suspension is filtered and washed with cyclohexane. The solid is dried, to obtain 9.55 g of compound (12). Yield 88.4%;

HPLC purity: 99.1%

$^1$H-NMR (DMSO-$d_6$, 300 MHz): δ (ppm) 1.02-1.79 (m, 12H), 1.31 (s, 9H), 2.07 (d. 2H), 2.74-2.78 (m, 2H), 2.88-2.96 (m, 3H), 3.22-3.33 (m, 3H), 3.80-3.83 (m, 2H), 4.01-4.20 (m, 1H), 6.88 (dd, 1H), 7.18-7.26 (m, 5H), 7.82 (broad singlet, 1H).

Example 5

(2-phenyl-1-(R)-((1-(tetrahydropyran-4-ylmethyl)-piperidin-4-ylmethyl)-carbamoyl)-ethyl)-carbamic acid tert-butyl ester) (12) (Method C)

A solution of 10 g of Boc-D-Phe-OH, 4.6 ml of N-methylmorpholine and 80 ml of dichloromethane is cooled to between −5° C. and 0° C., and a solution of 5.4 mL of isobutyl chloroformate in 20 mL of DCM is dripped into it at a rate such that the inner temperature does not exceed 5° C. The reaction mixture is kept under stirring at 0° C. for 1.5 hours. A solution of 8.7 g of compound (II) in 20 mL of dichloromethane is then added at a rate such that the inner temperature does not exceed 5° C. The solution obtained is left under stirring for approx. 1 h at 0° C., and approx. 2 h at ambient temperature.

100 mL of 1M NaOH is added to the reaction mixture, and the two phases are separated after stirring. The organic phase is washed with $H_2O$ (2×), and after a low-pressure solvent change with ethyl acetate, compound (12) is isolated and purified by crystallisation from ethyl acetate, to obtain 14.44 g of white solid. Yield 84%.

HPLC purity: 98%.

Example 6

(2-phenyl-1-(R)-((1-(tetrahydropyran-4-ylmethyl)-piperidin-4-ylmethyl)-carbamoyl)-ethyl)-carbamic acid tert-butyl ester (12) (Method D)

A solution consisting of 10 g of Boc-D-Phe-OH, 40 ml of dichloromethane and 4.6 ml of N-methylmorpholine is slowly dripped into a solution of 5.4 ml of isobutyl chloroformate in 60 ml of dichloromethane cooled to 0° C., at a rate such that the inner temperature does not exceed 5° C. The resulting mixture is maintained under stirring at 0° C. for 1 hour. A solution consisting of 8.0 g of (11) in 20 ml of dichloromethane is dripped into the reaction mixture at a rate such that the temperature does not exceed 5° C. The solution is maintained under stirring at 0° C. for 1 hour, and at ambient temperature for 5 hours. After a process control, 100 ml of 1M NaOH is added to the mixture, the two phases are separated, the organic phase is washed with water (2×), and after a low-pressure solvent change with ethyl acetate compound (12) is crystallised from ethyl acetate, to obtain 14.29 g of white solid. Yield 83%.

HPLC purity 98%.

Example 7

(2-phenyl-1-(R)-((1-(tetrahydropyran-4-ylmethyl)-piperidin-4-ylmethyl)-carbamoyl)-ethyl)-carbamic acid tert-butyl ester (12) (Method E)

A solution consisting of 10 g of Boc-D-Phe-OH, 40 ml of tetrahydrofuran and 4.6 ml of N-methylmorpholine is slowly dripped into a solution of 5.4 ml of isobutyl chloroformate in 60 ml of tetrahydrofuran cooled to 0° C., at a rate such that the inner temperature does not exceed 5° C. The resulting mixture is maintained under stirring at 0° C. for 0.5 hours. A solution consisting of 8.0 g of (11) in 20 ml of tetrahydrofuran is then dripped into the reaction mixture at a rate such that the temperature does not exceed 5° C. The solution is maintained under stirring at 0° C. for 1 hour, and at ambient temperature for 5 hours. 100 ml of 1M NaOH is added to the mixture, and the tetrahydrofuran is evaporated at low pressure. The residue is taken up with dichloromethane and water; the organic phase is washed with water (2×), and after a solvent change with ethyl acetate at low pressure, compound (12) is crystallised from ethyl acetate to obtain 15 g of white solid. Yield 87%.

HPLC purity 97%.

Example 8

(2-phenyl-1-(R)-((1-(tetrahydropyran-4-ylmethyl)-piperidin-4-ylmethyl)-carbamoyl)-ethyl)-carbamic acid tert-butyl ester) (12) (Method F)

6.7 g of carbonyldiimidazole is added to a solution of 10 g of Boc-D-Phe-OH in 80 ml of dichloromethane, cooled to 0° C. The resulting solution is maintained under stirring at 0° C. for 1 hour. A solution consisting of 8.0 g of (11) in 20 ml of dichloromethane is then dripped into the reaction mixture at a rate such that the temperature does not exceed 5° C. The solution is maintained under stirring at 0° C. for 1 hour, and at ambient temperature for 2 hours. 100 ml of 1M NaOH is added to the mixture, the two phases are separated, the organic phase is washed with water (2×), and after a low-pressure solvent change with ethyl acetate, compound (12) is crystallised from ethyl acetate to obtain 14.64 g of white solid. Yield 85%.

HPLC purity 98%.

Example 9

(2-phenyl-1-(R)-((1-(tetrahydropyran-4-ylmethyl)-piperidin-4-ylmethyl)-carbamoyl)-ethyl)-carbamic acid tert-butyl ester) (12) (Method G)

6.7 g of carbonyldiimidazole is added to a solution of 10 g of Boc-D-Phe-OH in 80 ml of tetrahydrofuran, cooled to 0° C. The resulting solution is maintained under stirring at 0° C. for 1 hour. A solution consisting of 8.0 g of (11) in 20 ml of tetrahydrofuran is dripped into the reaction mixture at a rate such that the temperature does not exceed 5° C. The solution is maintained under stirring at 0° C. for 1 hour, and at ambient temperature for 1 hour. 100 ml of 1M NaOH is added to the mixture, and the tetrahydrofuran is evaporated at low pressure. Dichloromethane and water are added to the residue; the two phases are separated, the organic phase is washed with water (2×), and after a low-pressure solvent change with ethyl acetate, compound (12) is crystallised from ethyl acetate to obtain 14.73 g of white solid. Yield 85%.

HPLC purity 96%.

Example 10

(2-(R)-amino-3-phenyl-N-(1(tetrahydropyran-4-ylmethyl)-piperidin-4-ylmethyl)-propionamide (4)

35 g of product (12) is added to 110 ml of methylene chloride, and 155 ml of precooled 3M HCl is added in portions to the suspension obtained. The biphasic mixture is kept under stirring overnight. The aqueous phase is collected and further washed with methylene chloride. Methylene chloride (65 ml) is then added to the aqueous phase, and after cooling to approx. 0° C., 65 g of 32% NaOH is added in portions, the temperature being maintained at under 20° C. The separated aqueous phase is further extracted with methylene chloride (2×), and the combined organic phases are washed with water (2×).

The organic phase then undergoes a solvent change with cyclohexane at atmospheric pressure to a volume of approx. 250 ml. 35 ml of hot ethyl acetate is then added to the cyclohexane solution and, after seeding, the temperature is gradually reduced to ambient values.

The suspension is then maintained under stirring at 0° C. for 2 hours, and filtered. The solid is washed with the precooled 1:6 (v/v) mixture of ethyl acetate/cyclohexane solvents and dried, to obtain 26 g of crystallised (4).

Yield=94.7%.

HPLC purity=100%.

HPLC: column: Zorbax Eclipse XDB-CN, 3.5 μm, 150×4.6 mm, mobile phase: preformed $KH_2PO_4$ 20 mM at pH 7/$CH_3CN$: 62/38. Flow rate: 0.8 ml/min, detector: UV, λ=214 nm, injection volume: 20 μl, temperature: 25° C.; RT (12)=8 minutes.

$^1$H-NMR (DMSO-$d_6$, 400 MHz): δ (ppm) 0.92-1.78 (m, 14 H), 2.06 (d, 2H), 2.56-3.01 (m, 6H), 3.20-3.39 (m, 3H), 3.77-3.84 (m, 2H), 7.13-7.29 (m, 5H), 7.78 (bt, 1H).

TLC: Silica gel plate, eluent: methylene chloride/2M $NH_3$ in MeOH, 9:1 (v/v), detection of spots with iodine vapour. Rf (12)=0.4

$[\alpha]_D$=+ 31° (C=1%, Acetone)

Melting point: 98-100° C. (Kofler)

Example 11

1-[(6-methyl-benzo[b]thiophene-2-carbonyl)-amino] cyclopentanecarboxylic acid (16)

100 g of precursor (1) is dissolved hot in anhydrified toluene, and 0.4 ml of N,N-dimethylformamide is added in an inert atmosphere. The mixture obtained is then cooled to ambient temperature, and 72.6 g of oxalyl chloride is dripped at a rate such that the temperature does not exceed 30° C.

The reaction mixture is then stirred at ambient temperature for at least 2 hours and concentrated again, diluted with fresh toluene and concentrated once again, to obtain a toluene solution of the acid chloride of compound (I).

In a second flask, 73.4 g of cycloleucine is suspended in anhydrous toluene, and 219 g of bis-trimethylsilyl acetamide (BSA) is added slowly at a rate such that the temperature does not exceed 30° C. After 30 minutes at ambient temperature, the reaction mixture is cooled to 0° C. and the toluene solution of the acid chloride of compound (I) is added. The reaction mixture is then kept under stirring at ambient temperature for at least 5 hours, then cooled to 0° C., and 1.6 litres of a dilute solution of NaOH (containing 121 g of NaOH) is slowly added at a rate such that the inner temperature does not exceed 30° C. The biphasic mixture is stirred at ambient temperature for 30 minutes. The rich aqueous phase is washed with toluene (3×) and cooled to 0° C., and 0.46 litres of 6N HCl is slowly added at a rate such that the temperature does not exceed 20° C. The suspension formed is stirred at ambient temperature for at least 15 hours and at 0° C. for 1 hour, then centrifuged and washed with water (3×) and isopropyl alcohol. 146 g of compound (16) in the form of a white solid is obtained after drying. Yield: 93%.

HPLC purity: 95.2%

$^1$H-NMR (CDCl$_3$, 200 MHz): δ (ppm) 1.65-1.80 (m, 4 H), 2.0-2.2 (m, 4 H), 2.42 (s, 3 H), 7.25 (d, 1 H), 7.75-7.85 (m, 2 H), 8.12 (s, 1 H), 8.70 (s, 1 H), 12-13.5 (broad singlet, 1H).

MS (ESI, positive ions)), m/z: 326 [M+Na]$^+$, 304 [M+H]$^+$, 258, 175

Melting point: 214-217° C. (Kofler)

Example 12

2-(6-methylbenzo[b]thiophene-2-yl)-3-oxa-1-aza-spiro[4,4]non-1-ene-4-one (3) (Method A)

Compound (16) (58 g) is dissolved in tetrahydrofuran (575 ml), and N-(3-dimethylaminopropyl)-N'-ethyl carbodiimide hydrochloride (EDAC) (39.8 g), acetonitrile (575 ml) and N,N-diisopropylethyl amine (DIPEA) (26.8 g) are added. The reaction mixture is stirred at ambient temperature for 20 hours, and a solvent change is performed with acetonitrile to a final volume of approx. 330-380 ml. The suspension obtained is stirred at 0° C. for 3 hours and centrifuged, and the solid is washed with 100 ml of acetonitrile to obtain 51 g of compound (3) in the form of a white solid. Yield 94.4%.

Crystallisation of Compound (3)

The compound (3) thus obtained (51 g) is suspended in ethyl acetate and the mixture is heated to 55° C.; the solvent is then partly evaporated at low pressure to a residual volume of approx. 160 ml. The suspension is cooled to 0° C. for 1 hour and centrifuged. The suspension is then washed with ethyl acetate and dried under vacuum at 40° C. to give compound (3) in the form of a white solid. Yield: 87%.

HPLC purity=99.96%.

HPLC: Symmetry, C18, 3.5 μm, 100×4.6 mm, Mobile phase A=CH$_3$CN, Mobile phase B=10 mM K$_2$HPO$_4$ pH=6. Gradient elution is then performed with the following protocol:

| Time (min) | % ACN | % H2O |
| --- | --- | --- |
| 0 | 30 | 70 |
| 20 | 80 | 20 |
| 24 | 80 | 20 |
| 25 | 30 | 70 |
| 30 | 30 | 70 |

Flow rate: 1 ml/min, detector: UV, λ=280 nm, injection volume: 20 μl, temperature: 30° C., RT (3)=19 minutes Melting point: 161-163° C. (Kofler)

Example 13

2-(6-methylbenzo[b]thiophene-2-yl)-3-oxa-1-aza-spiro[4,4]non-1-ene-4-one (3) (Method B)

9.0 g of compound (16) is suspended in a flask in 117 ml of dichloromethane, and 4.95 ml of triethylamine is added; the solution thus obtained is cooled to approx. 0° C., and 5.81 ml of isobutyl chloroformate is slowly added. After 30 minutes' stirring at 0° C. the reaction mixture is then returned to ambient temperature and washed with 25 ml of 0.5 M HCl, 25 ml of saturated NaHCO$_3$, and 25 ml of water. The organic solution is evaporated at low pressure until dry, to obtain 8.07 g of (3) in the form of a white solid.

Yield 95.4%.
HPLC purity: 99.4%

Example 14

2-(6-methylbenzo[b]thiophene-2-yl)-3-oxa-1-aza-spiro[4,4]non-1-ene-4-one (3) (Method C)

10.0 g of compound (16) is suspended in 100 ml of absolute ethanol; the suspension obtained is cooled to 0° C., and 6.0 ml of triethylamine and 5.2 ml of isobutyl chloroformate are added at a rate such that the inner temperature does not exceed 5° C. After 1.5 hours the suspension is filtered and the solid washed with absolute ethanol (2×) and dried to give 8.36 g of compound (3) in the form of a white crystalline solid. Yield: 88.9%.

HPLC purity: 98.9%.

Example 15

6-methyl-benzo[b]thiophene-2-carboxylic acid (1) (Method A)

8.5 g of palladium on 5% wet charcoal (50% water) is added in an inert atmosphere to a mixture of 11.33 g of 3-chloro-6-methyl-benzo[b]thiophene-2-carboxylic acid (18), 135 ml of N,N-dimethylformamide, 15 ml of 3.3 M NaOH and 40 ml of methanol/water 9/1. After repeated vacuum-hydrogen cycles, the suspension is maintained under stirring in a hydrogen atmosphere at ambient temperature for 20-24 hours. The mixture is then rendered inert and filtered through a Celite bed, and the catalyst is washed with 150 ml of methanol. The filtrate is evaporated until dry; 500 ml of water and 40 ml of 1N HCl are added, and the solution is maintained under stirring for 1 hour. The suspension is filtered and the solid washed with 200 ml of water and dried. After drying, 8.71 g of compound (I) is obtained in the form of a white solid; yield=90.6%. HPLC purity=99.3%.

MS m/z: 191 (M−H)$^-$ $^1$H-NMR (DMSO-d$_6$, 600 MHz): δ (ppm) 13.35 (broad singlet, 1H), 8.04 (s, 1H), 7.88 (d, 1 H, J=8.2), 7.84 (s, 1 H), 7.30 (dd, 1 H, J=1.0 Hz, J=8.2 Hz).

Example 16

6-methyl-benzo[b]thiophene-2-carboxylic acid (1) (Method B)

A suspension of 0.745 g of palladium on 5% wet charcoal (50% water) in 5 ml of methanol is added in an inert atmosphere to a mixture of 1.133 g of 3-chloro-6-methyl-benzo[b]thiophene-2-carboxylic acid (18) in 17.5 ml of tetrahydrofuran, 5 ml of 1N NaOH and 17.5 ml of methanol. The suspension is then maintained under stirring in a hydrogen atmosphere at ambient temperature for 18-20 hours. The mixture is rendered inert and filtered through a Celite bed, and the catalyst washed with 30 ml of methanol. The filtrate is then evaporated until dry at low pressure, and 30 ml of 1N HCl and 150 ml of ethyl acetate are added to the residue. The organic phase is washed with brine (2×) and evaporated until dry. 0.927 g of compound (I) is obtained in the form of a white solid; HPLC purity=97%, yield=96.4%.

Example 17

6-methyl-benzo[b]thiophene-2-carboxylic acid (1) (Method C) (MeOH/water and ammonium formate)

A suspension of palladium on 5% wet charcoal (50% water) (1.065 g) and ammonium formate (2.52 g) in methanol (30 ml) is stirred for 20 minutes in an inert atmosphere; a solution of 2.52 g of ammonium formate in 5 ml of water and a solution consisting of 2.26 g of 3-chloro-6-methyl-benzo[b]thiophene-2-carboxylic acid (18), 70 ml of methanol and 10 ml of 1N NaOH is then added. The mixture is kept under reflux stirring in an inert atmosphere for 15 hours. 0.425 g of Pd/C (5% wet) is then added, and the reaction mixture is again maintained under reflux for 24 hours. The mixture is then cooled, diluted with methanol, filtered through a Celite bed, and the catalyst is washed with further methanol. The filtrate is then evaporated until dry at low pressure and the residue treated with 70 ml of 1N HCl and 250 ml of ethyl acetate. The organic phase is washed with brine (3×) and evaporated until dry, to obtain 1.82 g of compound (1) in the form of a white solid; HPLC purity=98.2%, yield=94.7%.

Example 18

Ibodutant (Method A)

4.43 g of (3), 5.64 g of (4) and 60 ml of ethyl acetate are introduced into a 250 ml flask in an inert atmosphere; the suspension obtained is then heated and kept under reflux for 15 hours. The suspension is then filtered and the solid washed with ethyl acetate (2×) and dried to give 19.81 g of ibodutant in the form of a white solid.

Corrected yield: 98%
HPLC purity: 99.7%
$^1$H-NMR (DMSO-$d_6$, 300 MHz): δ (ppm) 0.99-1.15 (m, 4H), 1.30-1.44 (m, 1H), 1.44-1.84 (m, 13H), 1.85-1.95 (m, 1H) 1.85-1.95 (m, 1H), 1.97-2.08 (d, 2H, J=7.2 Hz), 2.24 (dt, 1H, J=13.2 e 8 Hz), 2.46 (s, 3H), 2.65-2.77 (d, 2 H, J=10.8 Hz), 2.85 (dd, 1H, J=14.0 e 10.8 Hz), 2.91-3.01 (m, 2H), 3.19 (dd, 1H, J=14.0 e 4.0 Hz), 3.22-3.31 (m, 2H), 3.81 (d, 2H, J=10.8 Hz), 4.41-4.51 (m, 1H), 7.08-7.25 (m, 5H), 7.29 (d, 1H, J=8.4 Hz), 7.48 (t, 1H, J=5.6 Hz), 7.82 (s, 1H), 7.84-7.90 (m, 2H), 8.24 (s, 1H), 8.82 (s, 1H).

HPLC: Symmetry, C18, 3.5 μm, 100×4.6 mm, Mobile phase A=CH$_3$CN, Mobile phase B=K$_2$HPO$_4$ 20 mM pH=2.2/CH$_3$CN 65/35. Gradient elution is performed with the following protocol:

| Time (min) | % A | % B |
|---|---|---|
| 0 | 0 | 100 |
| 7 | 0 | 100 |
| 20 | 77 | 23 |
| 25 | 77 | 23 |
| 26 | 0 | 100 |
| 30 | 0 | 100 |

Flow rate: 1 ml/min, detector: UV, λ=220 nm, injection volume: 20 μl, temperature: 30° C., RT (ibodutant)=5 minutes
Melting point: 193-195° C. (Kofler)
MS (m/z): 645 (MH$^+$, 100%), 360 (20%), 286 (10%)
Single-crystal X-rays: see Altamura et al., Acta Crystallographica Section B, 2006, 62, 889-896.

Example 19

Ibodutant (Method B)

14.3 g of (16), 57 ml of N,N-dimethylformamide, 4.45 ml of DIPEA and 9.9 g of EDAC are introduced into a 100 ml flask. The mixture is kept under stirring at ambient temperature for 18 hours; 16.8 g of (4) and 4.05 ml of DIPEA are then added to the flask, and the resulting mixture is stirred at ambient temperature for 21 hours.

The reaction mixture is dripped into a solution of 0.5 M NaOH cooled to approx. 10° C. The suspension obtained is maintained under stirring at approx. 10° C. for 3 hours, then filtered and the solid washed with water.

The solid is then crushed with water and filtered again, washed with water and dried. 27.1 g of crude ibodutant in the form of a white solid is obtained; yield=90.1%, HPLC purity=98%.

Crystallisation of Ibodutant 27 g of ibodutant is solubilised in absolute ethanol at approx. 70° C., and the solution is then concentrated. The suspension is stirred at ambient temperature for approx. 3 hours and at 0° C. for approx. 15 hours, and filtered; the solid is washed with an ethanol/methyl-tert-butylether mixture=1/3. The solid is then dried under vacuum at 40° C. to constant weight, and 25.1 g of ibodutant is obtained. Crystallisation yield: 93%.

The product, which corresponds to the characteristics described in example 18, has an HPLC purity of 99.85%.

Example 20

Ibodutant (Method C)

3.0 g of compound (16) is suspended in a 100 ml flask in 39 ml of dichloromethane and 1.50 ml of triethylamine is added; the solution thus obtained is cooled to approx. 0° C., and 1.45 ml of isobutyl chloroformate is added. After 30 minutes' stirring at 0° C., the formation of compound (3), with an HPLC purity exceeding 99%, will be observed. The reaction mixture is then returned to ambient temperature and washed with 0.5 M HCl (2×) and water (2×). A solvent change is then performed with ethyl acetate at atmospheric pressure to a residual volume of approx. 40 ml; 3.56 g of compound (4) is added, and the mixture is reflux heated for 9 hours and overnight at 55° C. The suspension is then cooled to ambient temperature and filtered; the solid obtained is washed with ethyl acetate (2×) and stove-dried under vacuum at 40° C. to obtain 4.60 g of ibodutant, namely a yield of 72%. The product, which corresponds to the characteristics described in example 18, has an HPLC purity of 99.9%.

The invention claimed is:
1. Process for the preparation of the compound ibodutant

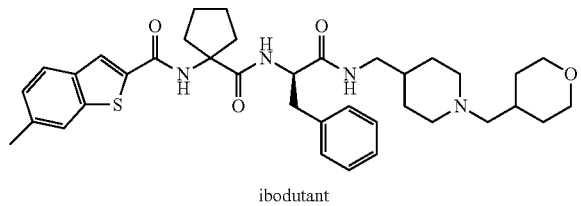 [SMILES: Cc1ccc2cc(C(=O)NC3(C(=O)N[C@H](Cc4ccccc4)C(=O)NCC4CCN(CC5CCOCC5)CC4)CCCC3)sc2c1]

ibodutant which comprises:

a) preparing the intermediate (12)

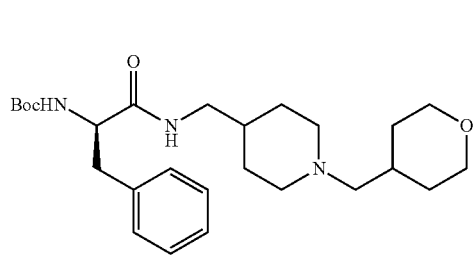
(12)

through the following steps:

a') protection of the primary amine of 4-aminomethyl-piperidine (2)

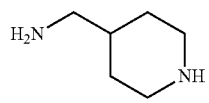
(2)

with ethyl-trifluoroacetate, followed by reductive amination of protected 4-aminomethyl-piperidine with 4-formyl-tetrahydropyran and a borane and by deprotection in basic medium to yield the intermediate diamine (11)

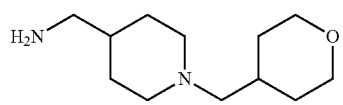
(11)

b') reaction of the diamine (11) with Boc-D-Phe to give the intermediate (12)

or alternatively through the following steps:

a") reaction between 4-aminomethyl-piperidine (2)

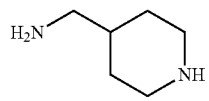
(2)

and Boc-D-Phe(OSu) to yield the intermediate (17)

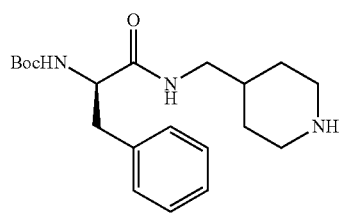
(17)

b") reductive amination of (17) with 4-formyl-tetrahydropyran and a borane to give the intermediate (12), b) deprotection of the intermediate (12) to yield (4)

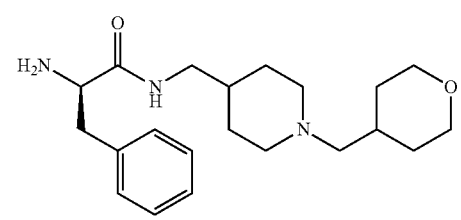
(4)

c) reaction between (4) and the compound (3)

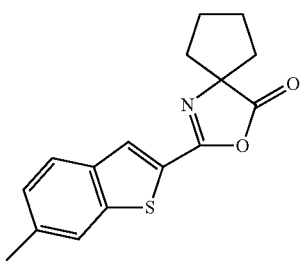
(3)

thereby obtaining the final product.

2. Process according to claim 1, wherein the reaction between compounds (3) and (4) in step c) is carried out in AcOEt as the solvent, for a time of 10 to 30 hours.

3. Process according to claim 1, wherein the borane Na(AcO)$_3$BH is used in the reductive aminations of steps a') and b").

4. Process according to claim 1, further comprising the crystallization of ibodutant in ethanol.

5. Process according to claim 1, further comprising the following steps for preparing compound (3):

a) activation of 6-methyl-2-benzo[b]thiophenecarboxylic acid of formula (1)

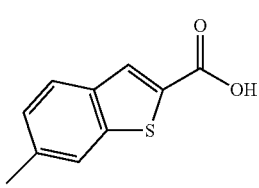
(1)

to the corresponding acyl chloride;

b) reaction between (1) and 1-amine-alpha,alpha-cyclopentane carboxylic acid to yield the intermediate (16)

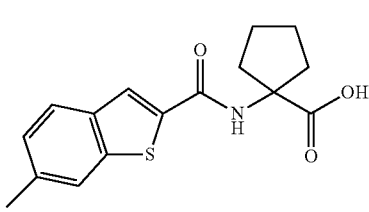
(16)

c) cyclization of (16) to the corresponding oxazolone of formula (3).

6. Process according to claim 5, further comprising the preparation of 6-methyl-2-benzo[b]thiophenecarboxylic acid (1) by means of catalytic hydrodehalogenation on Pd/C of 3-chloro-6-methyl-2-benzo[b]-thiophenecarboxylic acid (18)
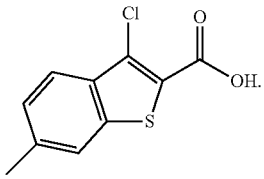
(18)
7. Process according to claim 1, wherein the oxazolone of formula (3) is obtained from (16) and immediately reacted, without isolation and purification, with intermediate (4) to give the final product ibodutant.
* * * * *